(12) United States Patent
Owen et al.

(10) Patent No.: US 6,486,474 B1
(45) Date of Patent: Nov. 26, 2002

(54) INFRARED SPECTROMETER FOR THE MEASUREMENT OF ISOTOPIC RATIOS

(75) Inventors: Christopher J. Owen; Eugene Tokhtuev; Anatoly Skirda; Robert M. Carlson; Alexander Tokhtuev; Viktor Slobodyan, all of Duluth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/374,719

(22) Filed: Aug. 13, 1999

(51) Int. Cl.[7] ................................................. G01N 1/10
(52) U.S. Cl. .................. 250/339.02; 356/246; 356/244; 356/440
(58) Field of Search ..................... 250/339.02; 356/246, 356/440, 244

(56) References Cited

U.S. PATENT DOCUMENTS

| | | |
|---|---|---|
| 2,779,230 A | 1/1957 | White |
| 4,078,896 A | 3/1978 | Moen et al. |
| 4,225,232 A | 9/1980 | Boisde et al. |
| 4,934,816 A | 6/1990 | Silver et al. |
| 4,937,448 A | 6/1990 | Mantz et al. |
| 4,953,976 A | 9/1990 | Adler-Golden et al. |
| 5,317,156 A | 5/1994 | Cooper et al. |
| 5,422,485 A | 6/1995 | Bowlds |
| 5,444,528 A | 8/1995 | Puschell |
| 5,486,699 A | 1/1996 | Fabinski et al. |
| 5,515,859 A | 5/1996 | Paz |
| 5,726,752 A | 3/1998 | Uno et al. |
| 5,747,809 A | 5/1998 | Eckstrom |
| 5,787,885 A | 8/1998 | Lemelson |
| 5,807,750 A | 9/1998 | Baum et al. |

FOREIGN PATENT DOCUMENTS

| | | |
|---|---|---|
| DE | 40 02 436 A1 | 1/1990 |
| EP | 0 254 879 | 6/1987 |
| EP | 0 388 082 | 3/1990 |
| EP | 0 584 897 A1 | 7/1993 |
| WO | WO99/14576 | 3/1999 |

OTHER PUBLICATIONS $^{13}$C—Stable Isotope Diagnostics, Wagner Analysen Technik Product Literature, pp. 1–4. (In German with English translation).

$^{15}$NH$_4$ ·Excretion Test: A New Metod for Detection of Helicobacter Pylori Infection by, Jicong et al., Journal of Clinical Microbiology, vol. 30, No. 1, Jan. 1992, pp. 181–184.

"Isotope–Selective Concentration Measurement of Breath Gas with A NDIR Spectrometer" by, Haisch et al., Techniques, vol. 63, 1996. (In German with English translation).

"Mass Spectroscopy Detects Ulcer–Causing Bacteria", Biophotonics International—19, Jan./Feb. 1998.

*Primary Examiner*—Constantine Hannaher
*Assistant Examiner*—Andrew Israel
(74) *Attorney, Agent, or Firm*—Westman, Champlin & Kelly, P.A.

(57) ABSTRACT

An infrared spectrometer for the determination of isotopic ratios of gaseous compounds includes a broad-band infrared light source, a spectral selector, a sample compartment, an infrared detector, and a processor. The spectral selector selectively transmits a wavelength window of infrared light covering a range of wavelengths in which the wavelength window can be selected alternatively to overlap with a wavelength range primarily absorbed by a compound with a first isotope or by the compound with a second isotope. The sample compartment holds a gas sample and includes a gas inlet and a gas outlet. The infrared spectrometer can be used to detect isotopic ratios of carbon dioxide, where enhancement of $^{13}$CO$_2$ can indicate metabolic activity of an infection, for example by *H. pylori*, or of specific enzymes. Preferred embodiments use a particular multipass optical cell that includes a field mirror and a multi-segment objective mirror.

18 Claims, 9 Drawing Sheets

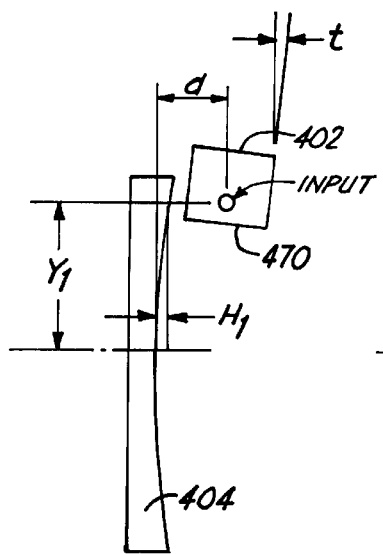
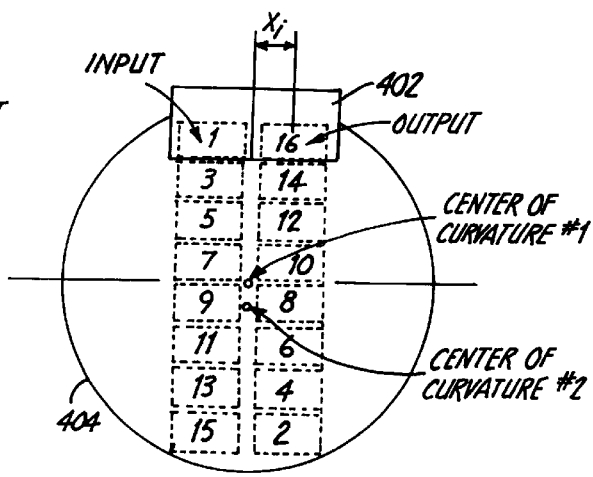
Fig. 11A
Fig. 11B
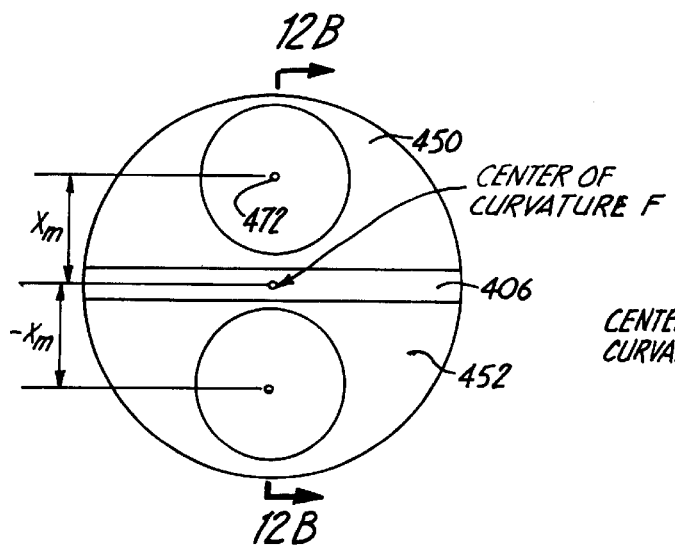
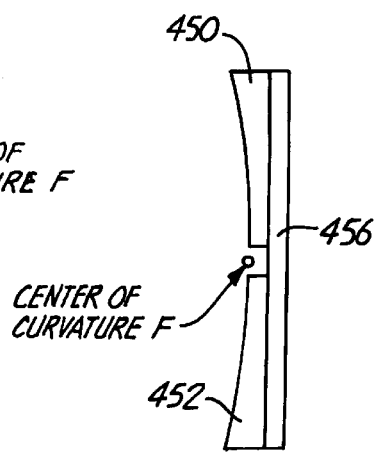
Fig. 12A
Fig. 12B

INFRARED SPECTROMETER FOR THE MEASUREMENT OF ISOTOPIC RATIOS

FIELD OF THE INVENTION

The invention relates to the spectroscopic evaluation of isotope ratios in a gas sample. More particularly, the invention relates to an infrared spectrometer with low spectral resolution for the evaluation of isotope ratios of an atom in a compound of a gas sample. The spectroscopic isotope analyzer is suitable for medical diagnostics.

BACKGROUND OF THE INVENTION

The evaluation of isotope ratios has applications in a variety of fields including chemistry, biology, geology and archeology. For example, $^{14}C$ dating has been used in geology and archeology to evaluate the age of dead biological tissue. Also, the measurement of stable isotopes can be used in biology to study metabolic processes. The measurement of isotope ratios have also found use in medicine for the evaluation of disease, especially diseases of the gastrointestinal tract.

Several human diseases of the gastrointestinal tract, such as gastritis and peptic ulcers, have been found in recent studies to be closely associated with bacterial infection by *Helicobacter pylori*. An estimated 4.5 million people in the U.S. annually suffer from peptic and gastric ulcers, of which about 80% are thought to be associated with *H. pylori*. In addition, the World Health Organization believes that over 80% of the population in developing countries may be infected with *H. pylori*. Furthermore, *H. pylori* is considered to be a Class I carcinogen that increases an infected person's risk of developing stomach cancer.

Blood tests can be used to detect factors associated with the infections, but blood tests do not indicate whether or not the infection is active. Metabolic activity of nonphotosynthetic cells generally involves the oxidation of organic compounds and the corresponding production of carbon dioxide. Thus, production of carbon dioxide is a direct indication of metabolic activity.

SUMMARY OF THE INVENTION

In a first aspect, the invention pertains to an infrared spectrometer for the evaluation of isotopic ratios in a gas sample, the spectrometer comprising:

a broad-band infrared light source, wherein light emitted by the light source proceeds along a light path;

a spectral selector placed along the light path, wherein the spectral selector selectively transmits a wavelength window of infrared light covering a range of infrared wavelengths, in which the wavelength window can be selected alternatively to overlap with a wavelength range primarily absorbed by a compound with a first isotope or by the compound with a second isotope;

a sample compartment for holding a gaseous sample, wherein the light path passes through the sample compartment, the sample compartment comprising a gas inlet and a gas outlet;

an infrared detector placed along the light path to receive infrared light after passing through the spectral selector and the sample compartment; and a processor connected to receive output from the infrared detector, wherein the processor evaluates a quantity related to the ratio of isotopes.

In another aspect, the invention pertains to a method for determining a quantity related to the isotopic ratio of a compound in a gaseous sample, the method comprising:

directing broad band infrared light through a gas sample;

selecting a first wavelength window by spectrally separating light from the broad band light source, wherein the first wavelength window overlaps with a wavelength range primarily absorbed by the compound with a first isotope;

selecting a second wavelength window by spectrally separating light from the broad band light source, wherein the second wavelength window overlaps with a wavelength range primarily absorbed by the compound with a. second isotope;

detecting infrared light in the first wavelength window following passage through the gas sample to obtain a first value of detected infrared light;

detecting infrared light in the second wavelength. window following passage through the gas sample to obtain a second value of detected infrared light; and evaluating a value related to the isotopic ratio of a compound in a gaseous sample from the values of detected infrared light.

In addition, the invention pertains to a multipass optical cell comprising:

a field mirror having a focal length and a center axis;

a two segment objective mirror generally facing the field mirror wherein the two segments are displaced from each other to move their respective focal points away from each other; and a prismatic mirror displaced from the field mirror by less than about 20 percent of the focal length of the field mirror, wherein the edge of intersecting faces of the prismatic mirror is generally oriented toward the objective mirror and wherein the plane bisecting the two faces of the prismatic mirror pass through the two segments of the objective mirror.

BRIEF DESCRIPTION OF THE DRAWINGS

FIG. 11A is a sectional side view of a field mirror and prismatic mirror of the multipass optical cell of FIG. 8, where the section is taken through the center of the mirror.

FIG. 11B is a front view of the field mirror of FIG. 11A, where sequential reflection points are numbered for one embodiment of the multipass optical cell.

FIG. 12A is a front view of a split objective mirror of a multipass optical cell of FIG. 8.

FIG. 12B is a sectional side view of the split objective mirror of FIG. 12A taken along line B—B.

DETAILED DESCRIPTION OF THE ILLUSTRATIVE EMBODIMENTS

Figure 1:
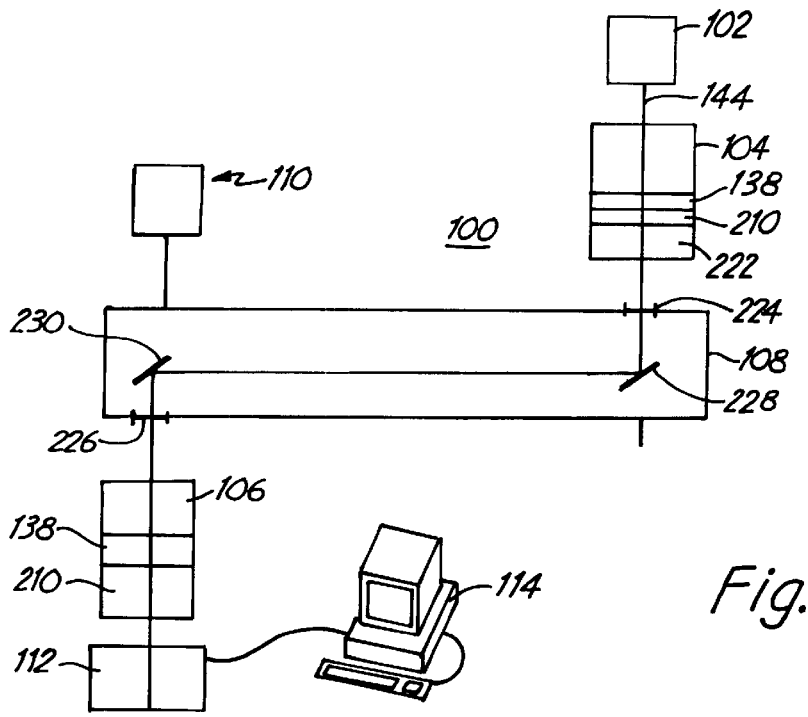
FIG. 1 is a schematic representation of an infrared spectrometer useful for the measurement of isotope ratios in a gas sample.

An infrared spectrometer for the evaluation of isotopic ratios of an atom within a compound of a gas sample transmits for detection selected wavelength windows of infrared light substantially absorbed by the compound with the one of the isotopes. The isotopic ratio can be evaluated extremely efficiency from the absorption measurements covering the different wavelength windows. A single gas sample is used for two or more measurements at least involving wavelength windows each covering wavelengths primarily absorbed by the compound with one of the isotopes. High precision and accuracy can be. obtained very quickly using low resolution spectroscopy, which averages over rotational structure in the spectrum. A low cost but highly effective multipass optical cell preferably is used as a sample compartment to greatly increase the sensitivity of the measurements.

The improved infrared spectrometer for isotope detection includes a broad band infrared light source, a sample compartment, infrared detector, a spectral selector that alternatively directs light within a wavelength window to the infrared detector and a processor. The light source initiates a light beam that passes through the sample compartment on the way to the infrared detector. The spectral selector can be placed between the light source and the sample compartment or between the sample compartment and the detector.

The evaluation of carbon dioxide isotopic ratios is of particular interest. Carbon dioxide generation can be indicative of metabolic activity by an organism. A substrate metabolized by an organism or cell type of interest can be isotopically enhanced such that carbon dioxide produced by the particular organism/cell can be distinguished from background carbon dioxide. The detection of *Helicobacter pylori* using $^{13}C$ enhanced urea is of particular interest, although other human diseases can be detected using other isotopically enhanced substrates, as described further below.

The spectral selector selectively transmits light alternatively within wavelength windows covering a range of infrared wavelengths to the infrared detector, which includes one or more light sensitive elements. One wavelength window overlaps with a wavelength range primarily absorbed by a compound in the gas sample with a first isotope, and a second wavelength window overlaps with a wavelength range primarily absorbed by the compound with a second isotope. By alternating between the wavelength windows, absorption by the compound with the different isotopes can be separately measured.

Alternation between wavelength windows can involve alternative transmission of the wavelength windows or alternative direction of the wavelength windows to separate light detectors or set of detectors. Additional wavelength windows can be used corresponding to reference wavelengths, wavelengths absorbed by other compounds and/or wavelengths absorbed by the compound of interest with the same two isotopes or additional isotopes. In the harmonic oscillator approximation, vibrational frequencies of the compound with different isotopes shift by the square root of the ratio of reduced masses. The reduced masses are functions of the atomic masses in which the functional relationship is determined by the features of the particular normal mode vibration.

In some preferred embodiments, the spectral selector includes a plurality of infrared filters that each selectively transmit wavelengths within a Specific desired wavelength window. The filters can be mounted on a wheel for easy selection of a desired filter by the rotation of the wheel. The temperature of the filters preferably is maintained within a narrow range since temperature fluctuations can alter the characteristics of the transmitted wavelength window. Alternatively, the spectral selector can include an optical element that spatially disperses the infrared light by wavelength. The wavelength window is selected by separately processing portions of the spatially separated light corresponding to the desired wavelength windows.

The infrared spectrometer and measurement approaches are designed for rapid, precise and accurate measurements. Using low resolution spectroscopy provides measurements that are less sensitive to fluctuations in temperature and pressure by averaging over rotational fine structure. Use of a spectral selector provides for rapid performance of multiple infrared measurements with a single gas sample. Since only a single gas sample is used, variations within the conditions between two gas samples are eliminated. Temperature and pressure within the gas sample is maintained approximately at selected values to fluctuations in the sample over the short time period of the measurements. Also, additional reference infrared absorption measurements can be performed on the single gas sample to perform a more accurate analysis of the isotope ratio.

The sensitivity of the infrared measurements can be increased significantly through the use of a multipass optical cell without the need to use an inconveniently large sample cell to obtain a large path length. The multipass cell reflects the infrared light a plurality of times, preferably many times, through the gas sample to increase the effective optical path length. Thus, a compact optical cell can be used to hold the sample. The cell is preferably designed with a gas inlet and outlet that allows for the efficient flushing and filling of the cell with relatively nonturbulent flow through the cell during the filling period. The cell preferably includes a pressure control that provides for the placement of the gas sample within the cell at a reproducible pressure for the measurement. The cell inlet preferably is connected to a dehumidifier for the removal of a significant amount of water from the sample prior to introduction into the sample cell to reduce background infrared absorption.

A preferred embodiment of a multipass optical cell includes a spherical field mirror, a split spherical objective mirror and a prismatic mirror. The spherical field mirror and split spherical objective mirror face each other within the sample cell. The split spherical objective mirror includes two portions of a spherical mirror that are spatially separated to shift the position of a reflected light spot on the spherical field mirror. The prismatic mirror is used to direct an incoming infrared beam toward the split mirror and out from the cell after a number of reflections between the two mirrors. This improved design of the multipass optical cell can be integrated conveniently into the overall design of the sample cell, although the multipass optical cells can be used in any of a variety of other optical systems that operate in the infrared or over other wavelength ranges.

Preferred uses of the infrared spectrometer include the measurement of the ratio of $^{13}C^{16}O_2$ to $^{12}C^{16}O_2$. The known vibrational absorption spectrum of carbon dioxide is used to select appropriate infrared absorption windows that are relatively free from interfering infrared absorption by other species within a gas sample from the breath of a patient. In particular, gas/breath samples from a human patient have relatively predictable ranges of gas species, including molecular oxygen, nitrogen, water, carbon dioxide and other compounds in small quantities, many of which do not significantly absorb infrared light.

If a $^{13}C$ enhanced substrate is used to detect metabolic activity by a specific agent, the carbon dioxide measured in the gas sample will have a $^{13}C^{16}O_2/^{12}C^{16}O_2$ ratio that is larger than the corresponding ratio in naturally occurring organic compounds and carbon dioxide. An increase in the $^{13}C^{16}O_2/^{12}C^{16}O_2$ ratio indicates the suspected metabolic activity is present. Even using isotopically enhanced substrates, measurements of modification of the isotopic ratio generally requires high sensitivity to detect accurately shifts in the isotopic ratio above background levels of natural carbon dioxide.

A. Spectrometer For Isotope Ratio Measurement

Referring to FIG. 1, an infrared spectrometer 100 for relative isotope measurements in a gas sample includes a broad band infrared light source 102, a first set of optical components 104, a second set of optical components 106, a gas sample cell 108, a gas regulation apparatus 110, an infrared detector-112 and a processor 114. Three particular embodiments 120, 122, 124 of the spectrometer 100 are shown schematically in FIGS. 2–4.

Figure 2:
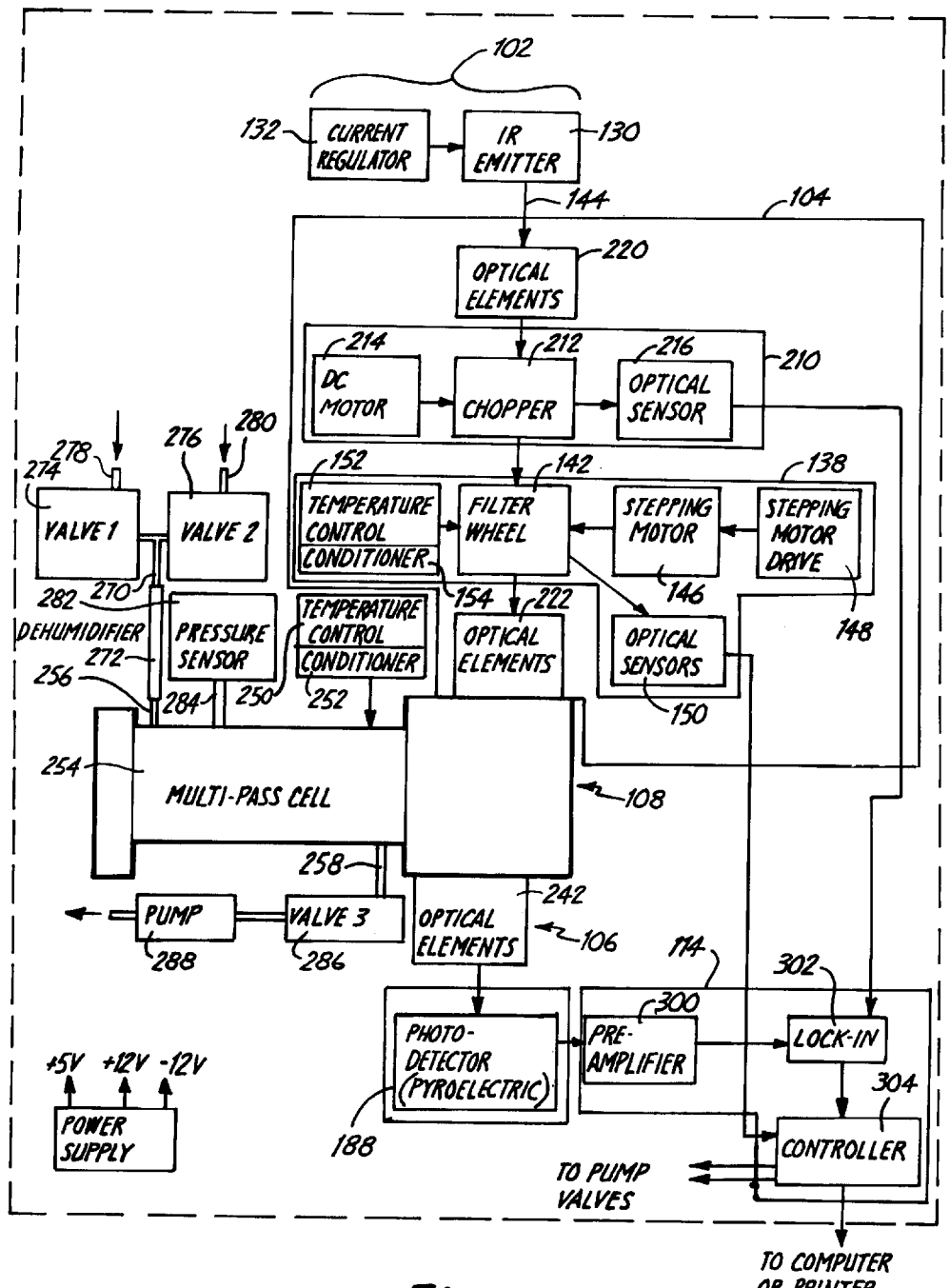
FIG. 2 is a schematic diagram of an embodiment of an infrared spectrometer configured for the measurement of isotope ratios of gas samples.
Figure 3:
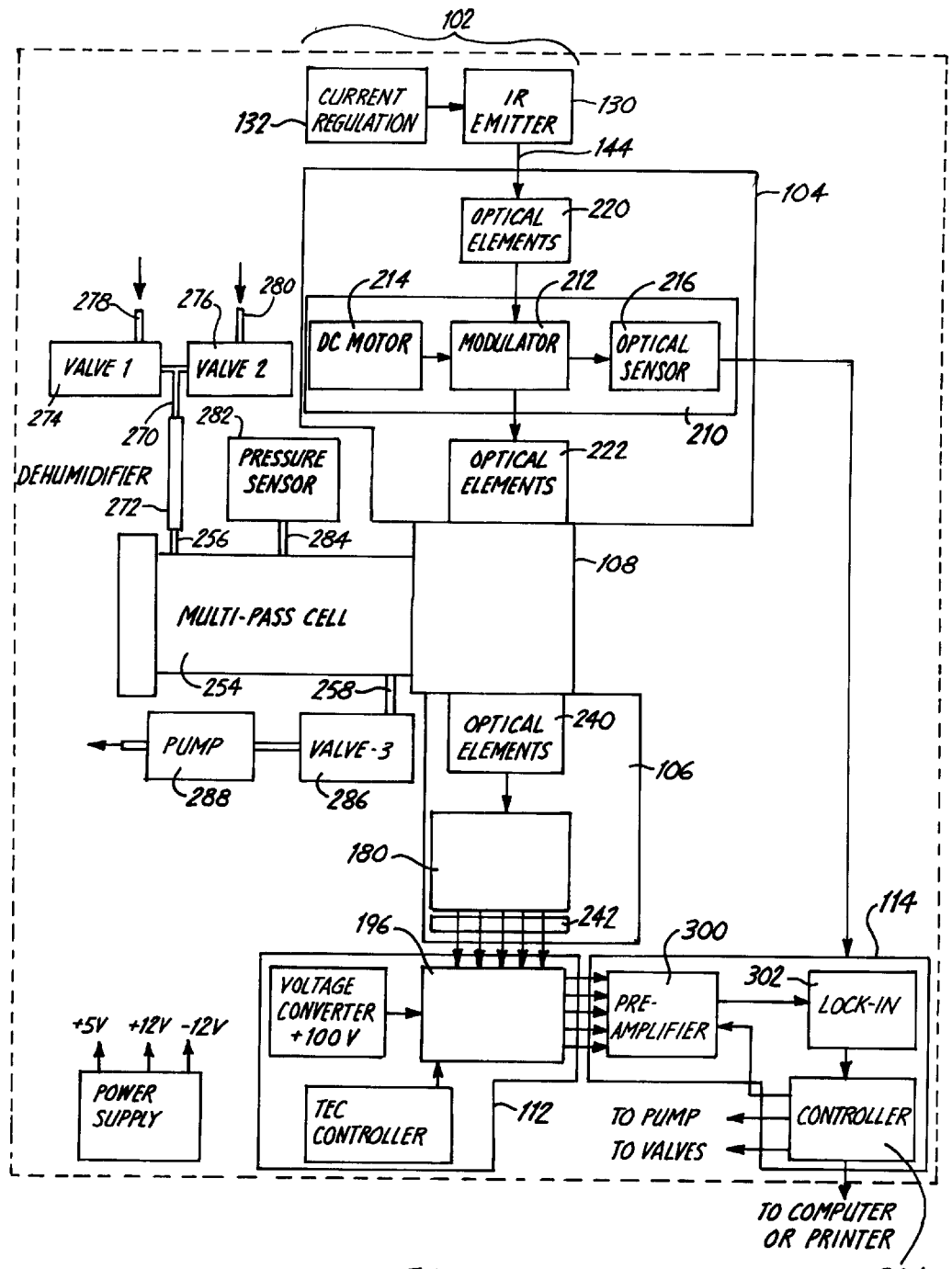
FIG. 3 is a schematic diagram of an alternative embodiment of an infrared spectrometer configured for the measurement of isotope ratios of gas samples.

Infrared source 102 can be any suitable source with emissions covering all the wavelengths of interest. Referring to FIGS. 2 and 3, infrared source 102 can include an infrared emitter 130 and current regulator 132. Infrared emitter 130 can be; for example, a glo-bar or other steady state emitters, such as the LC-IR-12 emitter (9W, 3.9×3.6 mm), CS-IR-21V emitter (4W, 1.5×3.2 mm) both from Toma Tech, Ltd. and SA105010-8M2 emitter from Cal Sensors, Inc., Santa Clara, Calif. Pulsed emitters are also available from Cal Sensors, Inc. with modulation frequencies up to about 10 Hz. Pulsed emitters can be used in place or separate emitters and a modulator, although a separate modulator can be used to obtain higher modulation frequencies. Current regulator 132 is used to obtain stable emission intensity from emitter 130.

Optical components 104, 106 serve several functions. First, first optical components 104 focus the infrared light and direct the light to sample cell 108. Second optical components 106 receive the light from the sample cell 108 and focus and direct the light onto the detector 112, as shown in FIG. 1. Also, optical components 104, 106 preferably modulates the light beam to permit lock-in amplification. In addition, optical components 104, 106 include spectral selector 138 that spectrally separates the infrared light. Generally, either optical components 104 or optical components 106 includes a spectral selector 138.

If spectral selector 138 is associated with optical components 104, light transmitted into cell 108 ranges over a selected wavelength window. Alternatively, if spectral selector 138 is associated with optical components 106, broad band infrared light is transmitted through cell 108 and spectral selection takes place between cell 108 and detector 112. Spectral selector 138 provides for the alternative detection of absorption by the gas sample at least over a first infrared wavelength window overlapping with a wavelength range absorbed primarily by a specific compound with a first isotope and a second wavelength window overlapping with a wavelength range absorbed primarily by the compound with a second isotope.

Figure 4:
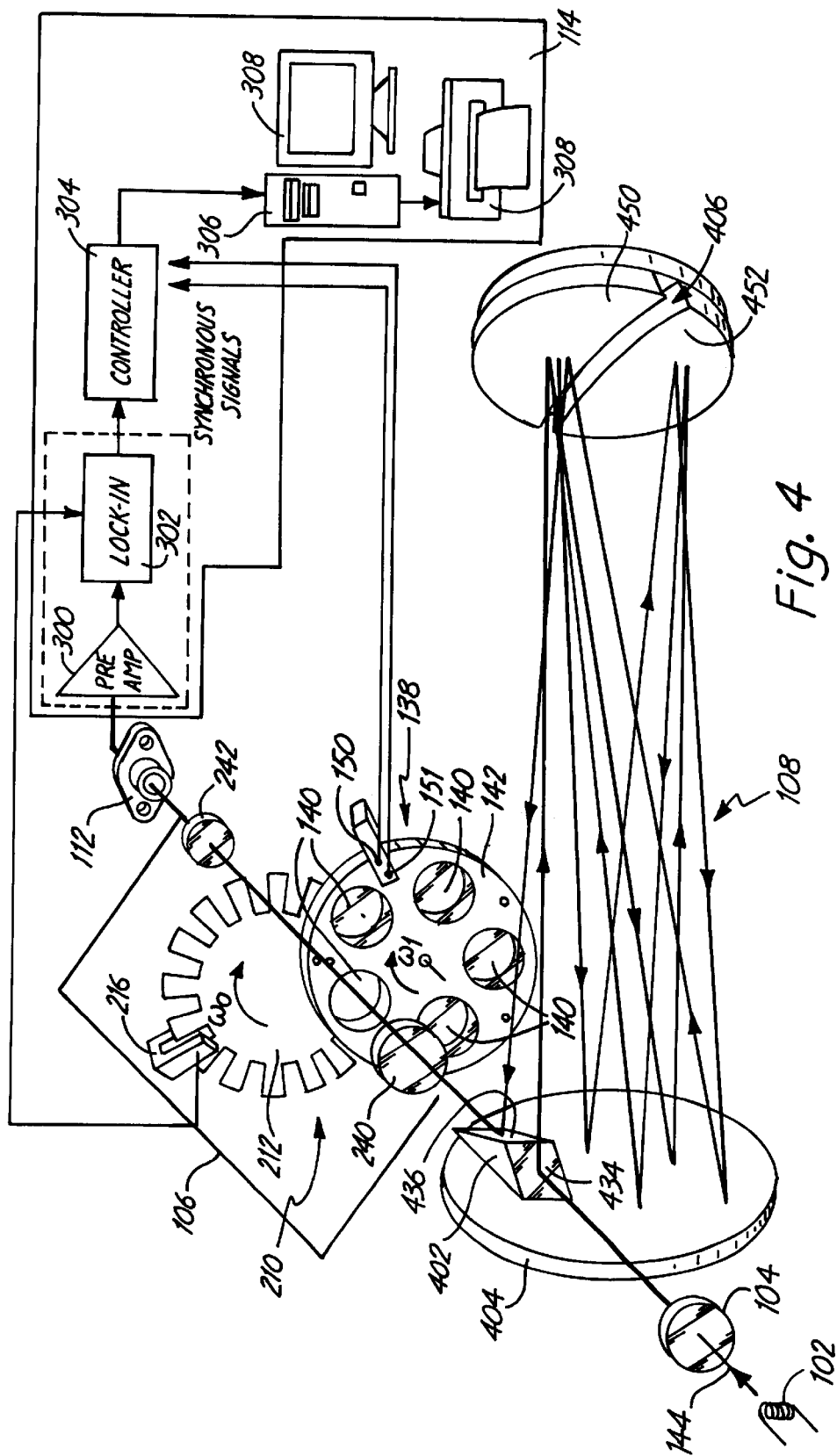
FIG. 4 is a schematic perspective view of a portion of another alternative embodiment of an infrared spectrometer configured for the measurement of isotope rations of gas samples.

Referring to FIGS. 2 and 4, an embodiment of spectral selector 138 includes a plurality of optical filters 140. Each optical filter is selected to transmit infrared light in a wavelength window covering a relatively narrow wavelength range. For convenience, optical filters 140 can be mounted on a filter wheel 142 (FIGS. 2 and 4) such that they can be rotated into and out from the light path 144 from infrared source 102. Filter wheel 142 can be rotated precisely using a stepper motor 146 and a stepper motor drive 148 or other suitable motor.

In preferred embodiments, at least two optical sensors 150, 151 are placed around filter wheel 142 to monitor the passage of filters 140 as wheel 142 is rotated. One optical sensor monitors the correct location of each optical filter while the other sensor monitors the introduction of the first filter into the light path. Thus, the position of the wheel can be controlled by processor 114, described further below. Each optical sensor includes an infrared emitter and an infrared detector. Suitable optical sensors include, for example, OMRON® non-amplified optical sensors distributed by Digi-Key Corp., Thief River Falls, Minn.

Filters 140 are susceptible to temperature fluctuations. The transmission properties of the filters generally depend on the temperature of filters 140. Thus, considerably more precise and accurate measurements are obtained if the temperature of filters 140 is maintained within a particular narrow temperature range. A temperature controller 152 is used to monitor the temperature using a temperature sensor located within the filter housing, and a temperature conditioner 154 is used to heat and/or cool the filter to maintain a desired temperature range. In preferred embodiments, temperature conditioner 154 has a heater located within the filter wheel housing. The heater can be produced from a power transistor. Interference filters can be ordered with transmission windows standardized to about 40° C., which is a convenient temperature to maintain the filters.

In one embodiment, preferred filters are narrow band interference filters. Suitable infrared interference filters are available from Spectragon US, Inc. A suitable set of filters for carbon dioxide measurement include filters NB-2580-050-D (primarily $H_2O$ absorption), NB-2670-050-D (primarily $^{12}CO_2$ absorption), BP-3900-110-D (reference filter) and NB-4420-050-D (primarily $^{13}CO_2$, special order).

Figures 5A, 5B:
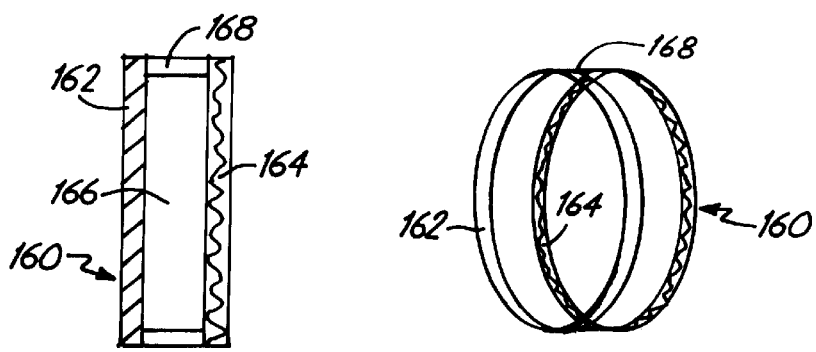
FIG. 5A is a side view of a combination filter with a gas cell and an interference filter.
FIG. 5B is a perspective view of the combination filter of FIG. 5A.

In alternative preferred embodiments, the filters are gas filled filters that include a selected gas between two windows. These gas filled filters generally are combined with corresponding interference filters to form combination filters. Referring to FIGS. 5A and 5B, combination filter 160 includes a window 162 and an interference filter 164, which form the front and back surfaces of a gas cell 166. A band 168 encircles window 162 and interference filter 164 to enclose gas cell 166. The gas in gas cell 166 absorbs infrared light inside of the desired wavelength transmission window to increase the necessary filtering performed by the corresponding interference filter. The concentration of gas in the filter can be adjusted to approximately absorb an equivalent amount of light as the corresponding gas in the sample cell. Parameters for five suitable combination filters are presented in Table 1.

TABLE 1

| # | gas % $^{12}CO_2$ | gas % $^{13}CO_2$ | gas % $N_2$ | Cell Length mm | Pressure kPa | Interference filter microns |
|---|---|---|---|---|---|---|
| 1 | 99–50 | 0.5–1 | 0–49.5 | 5–10 | 50–100 | 2.54–2.65 |
| 2 | — | — | — | — | — | 2.66–2.79 |
| 3 | 50–20 | 0.5–0.2 | 49.5–79.8 | 5–10 | 50–100 | 4.34–4.52 |
| 4 | 50–20 | 50–80 | — | 5–10 | 50–100 | 4.34–4.52 |
| 5 | — | — | — | — | — | 3.85–3.95 |

Combination filter 1 can be used to obtain water absorption measurements with reduced influence from $^{12}CO_2$. Filter 2 gives direct measurement of $^{12}CO_2$. Filters 3 and 4 provides the measurement of the enhanced amount of $^{13}CO_2$ with less interference from $^{12}CO_2$ and background levels of $^{13}CO_2$. Filter 5 is used as reference filter.

The plurality of spectral filters includes at least one filter that transmits in a spectral window overlapping a wavelength range primarily absorbed by a compound with a first isotope and a second filter that transmits in a spectral window overlapping a wavelength range primarily absorbed by the compound with a second isotope. In preferred embodiments, additional filters are included. For example, an optical filter can be included as a reference filter that transmits infrared light in a wavelength window covering wavelengths with little absorption by gas species within cell 108.

Similarly, an optical filter can be included that transmits a wavelength window covering wavelengths absorbed primarily by water, a strong infrared absorber. Approximate quantification of water vapor can be used to correct absorption values for other compounds in the gas sample at other wavelengths. Thus, correction for water vapor can be used to obtain more accurate isotope ratio values. Furthermore, additional optical filters can be included that transmit a wavelength window covering other wavelength ranges absorbed primarily by the compound containing one of. the two isotopes or with different isotopes. Below, the calculation of the isotope ratio based on absorption measurements at these possible wavelengths is described in more detail. Preferably, lenses are used to focus the incident light inside the interference filter to yield the narrows band width from the filter.

For the measurement of $^{13}C^{16}O_2/^{12}C^{16}O_2$ ratios in a gaseous breath sample, suitable filters include a first filter transmitting over a wavelength window centered between about 4.36 microns and about 4.46 microns corresponding to absorption primarily by $^{13}C^{16}O_2$, and preferably over a wavelength window spanning the range from about 4.36 microns and about 4.46 microns. Similarly, a second suitable filter transmits over a wavelength window centered between about 4.18 microns and about 4.25 microns corresponding to absorption primarily by $^{12}C^{16}O_2$, and preferably over a wavelength window spanning the range from about 4.18 microns to about 4.25 microns. Furthermore, a filter can be included that transmits over a wavelength window centered between about 2.54 to about 2.65 corresponding to absorption primarily by water, and preferably over a wavelength window spanning the range from about 2.54 microns to about 2.65 microns. Similarly, for the detection of carbon dioxide in a breath sample, a reference filter can be included that transmits over a wavelength window centered between about 3.85 microns and about 3.95 microns, between about 2.95 microns and about 3.05 microns or between about 3.55 microns and about 3.65 microns. A particularly preferred embodiment includes the four preferred filters described above in this paragraph.

Figure 6:
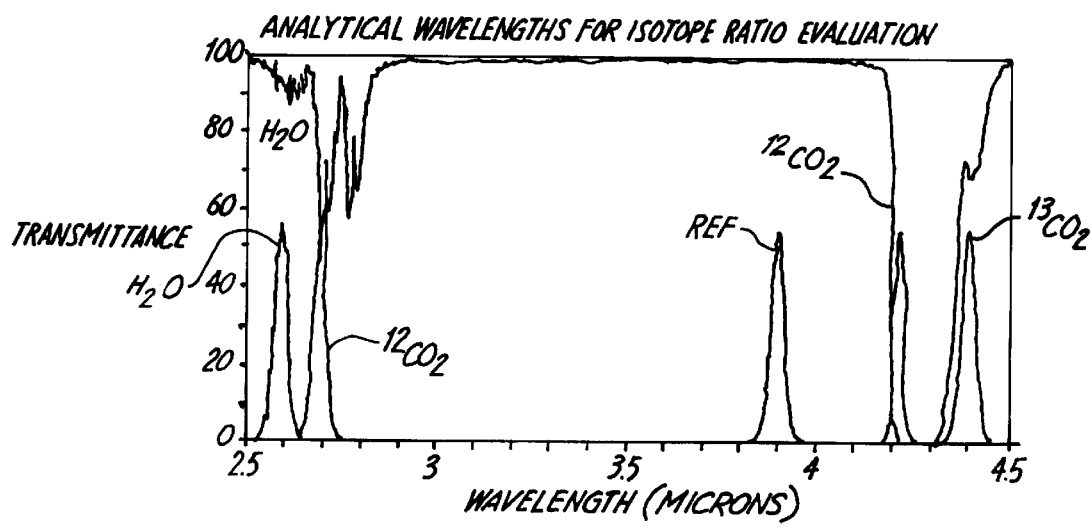
FIG. 6 is a plot of suitable wavelength windows corresponding to preferred filters for the evaluation of a ratio of $^{13}C^{16}O_2$ to $^{12}C^{16}O_2$ along with a plot of the infrared transmission spectrum of a breath sample.

Alternatively or in addition to the use of the filter transmitting over the absorption band of $^{12}C^{16}O_2$, a filter can be included that transmits over an wavelength window centered between about 2.66 microns and about 2.79 microns corresponding primarily to absorption by $^{12}C^{16}O_2$ and preferably over a wavelength window spanning the range from about 2.66 microns to about 2.79 microns. Another preferred combination of filters includes the five filters described above in this paragraph and the previous paragraph. The transmission bands of these five filters are plotted schematically in FIG. 6 along with a plot of the absorption spectrum of a breath sample from a human patient.

Alternative to the use of filters to perform the spectral separation, a dispersive element can be used to spatially separate the infrared light according to wavelength. Suitable dispersive elements include, for example, diffraction gratings and prisms. Where a dispersive element is used to spatially disperse the infrared beam by wavelength, selection of a desired spectral window then corresponds to the direction of a spacial extension of the dispersed light beam covering the desired spectral window to a light sensitive element in the detector. The dispersive element, the detector and optics are configured to have low spectral resolution to cover a wavelength window that sums over rotational structure of the spectrum while spanning a range of infrared wavelengths primarily absorbed by the compound of interest with a particular isotope. Suitable wavelength windows cover a wavelength range covering a span of from about 0.02 microns to about 0.30 microns, and preferably are around 0.10 microns.

Figure 7A:
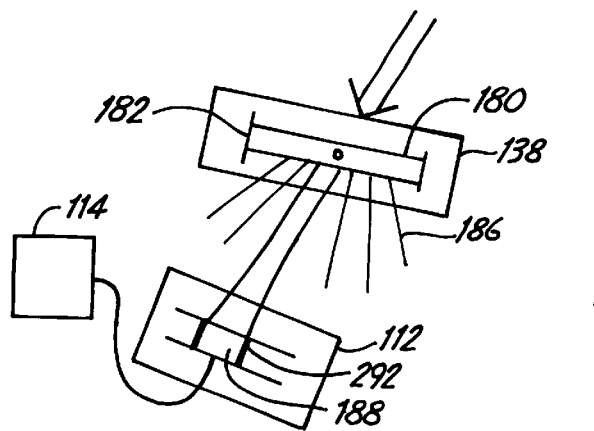
FIG. 7A is a schematic view of an embodiment of a spectral selector with a dispersive optical element and a single infrared detector element.

Spectral selector 138 including a dispersive element 180 is shown in FIG. 3. Referring to FIG. 7A, in a first embodiment of spectral selector 138 with dispersing element 180, dispersing element 180 is positioned on a pivoting mount 182. Pivoting mount 182 provides for a spacial shifting of the spatially dispersed infrared light 186 such that the light striking a detector element 188 can be selected to fall within a particular wavelength window. In this embodiment, detector 112 generally includes a single light sensitive detector element 188 or a set of adjacent detector elements to detect a wavelength window over a selected wavelength range.

Figure 7B:
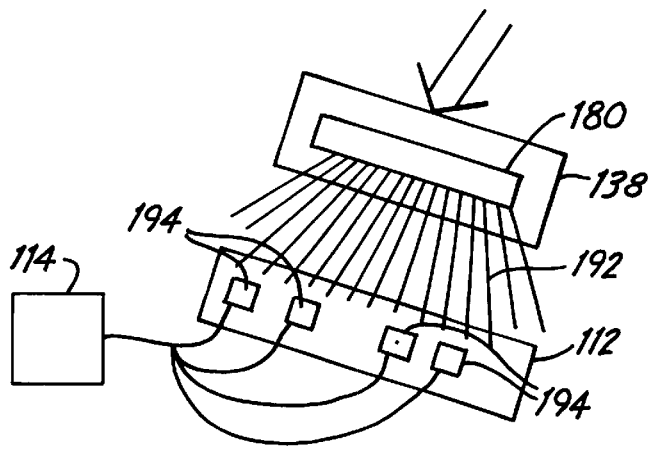
FIG. 7B is a schematic view of an embodiment of a spectral selector with a dispersive optical element and a plurality of infrared detector elements configured to detect selected wavelength windows.

An alternative embodiment of spectral selector 138 is shown in FIG. 7B. Spectral selector 138 includes a light dispersing element 180 with a fixed orientation that directs an infrared beam 192 spatially dispersed by wavelength toward detector 112. In this embodiment, detector 112 preferably includes a plurality of light sensitive elements 194 or adjacent groups of detector elements where each detector element 194 or adjacent group of detector elements is positioned to detect a particular wavelength window. This embodiment involves the simultaneous measurement of a plurality of desired spectral wavelength windows.

Figure 7C:
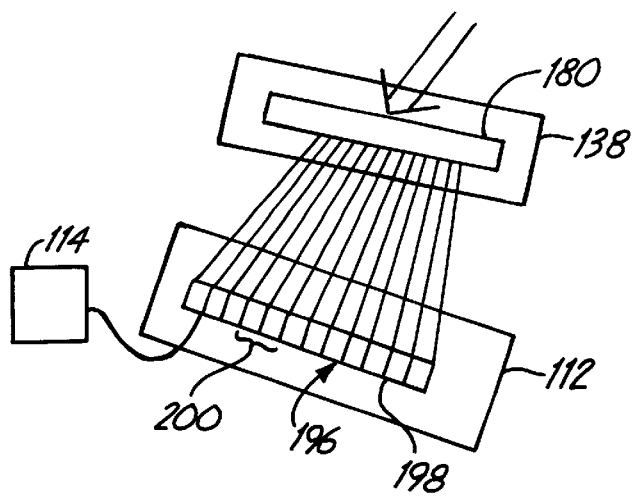
FIG. 7C is a schematic view of an embodiment of a spectral selector with a dispersive optical element and a detector array configured to detect selected wavelength windows.

The embodiment in FIG. 7C is similar to the embodiment in FIG. 7B except that detector elements 194 are replaced with detector array 196. Detector array 196 is configured such that a light sensitive element 198 or group of adjacent light sensitive elements 200 are positioned to detect a selected wavelength window. The embodiment in FIG. 7C has the advantage that the apparatus can be used to measure isotopes of different chemical compounds without modifying the hardware.

Referring to FIG. 1, optical components 104, 106 preferably include a modulator 210, which can be within either optical components 104 or optical components 106, as shown in FIG. 1. Modulator 210 modulates the signal with a specific period for lock-in amplification, to reduce noise and correspondingly increase the signal-to-noise ratio. Referring to FIGS. 2–4, modulator 210 generally includes a chopper wheel 212, a motor 214 to drive the chopper wheel 212 and an optical sensor 216 to time the lock-in amplification. Motor 214 can be, for example, a DC-motor or a stepper motor. Optical sensor 216 includes an IR emitter and an IR sensitive detector element. Suitable interrupter type optical sensors are available from Digi-Key Corp, Thief River Falls, Minn. Thus, chopper wheel 212 modulates the infrared light by intermittently breaking and transmitting the light beam at a period determined by the rotational speed of the wheel 212. Wheel 212 is rotated at a constant rotational speed to produce a modulation at a desired frequency. Output from optical sensor 216 is used to adjust the phase of the modulation used by the lock-in amplifier. If a pulsed infrared emitter, as described above, is used to modulate the infrared beam, an internal signal from the pulsed emitter can be used to set the phase of the modulation at the lock-in amplifier, where the phase is adjusted for any time delay associated with the internal signal of the emitter.

Generally optical components 104, 106 include additional optical elements such as mirrors, lenses and the like for directing and focusing the infrared beam, as depicted schematically in FIGS. 2–4. Referring to FIGS. 2–3, a first set of optical elements 220 direct and focus the infrared beam onto spectral selector 138 and/or modulator 210 if optical components 104 include spectral selector 138 and/or modulator 210. A second set of optical elements 222 preferably directs the infrared beam into sample cell 108 and focuses the infrared beam within sample cell 108. In some embodiments, the infrared beam is directed straight through sample cell 108. Alternatively, sample cell 108 can include mirrors and windows that provide for alternative orientations of sample cell 108 relative to the other components.

Referring to FIGS. 3 and 4, third set of optical elements 240 direct and focus the infrared beam onto spectral selector 138 and/or modulator 210 if optical components 106 include spectral selector 138 and/or modulator 210. Referring to FIGS. 2–4, a fourth set of optical elements 242 can be used to direct and 20 focus the infrared beam onto detector 112. Optical components 104, 106 can further include shutters, slits and other optical elements.

Lenses for infrared light can be produced from calcium fluoride or magnesium fluoride. These materials have low refractive indices to yield minor reflective losses from the lens surfaces. To obtain the highest efficiencies for the lenses, a radius of curvature of 15 mm for calcium fluoride lenses and 12.38 mm for magnesium fluoride lenses can be used.

Referring to FIG. 1, infrared beam 144 is directed through sample cell 108. Sample cell 108 can be configured such that infrared beam 144 directed passes through a window 224 at one end of sample cell 108 through a window 226 the other end of sample cell 108. Windows 224, 226 are at least partially transparent to infrared light and preferably are curved to reduce interference from reflections from the window surfaces. Sample cell 108 can include a first mirror 228 that redirects the infrared beam through sample cell 108 and a second mirror 230 that redirects the infrared beam from sample cell 108, as shown in FIG. 1. Using mirrors 228, 230 to direct infrared beam 144 into and out from sample cell 108, sample cell 108 can be turned to construct a more compact spectrometer. Sample cell 108 can include additional mirrors to direct infrared beam 144 within cell 108.

In preferred embodiments, sample cell 108 is a multipass optical cell that directs infrared beam 144 through the gas sample a plurality of times. Using a multipass optical cell effectively increases the optical path through the cell and increases absorption of the beam by the gas sample. For example, sample cell 108 can be a commercially available multipass optical cell. In a preferred embodiment of a multipass optical cell, described in detail below, first mirror 228 and second mirror 230 are two faces of a prismatic mirror, and the infrared beam is initially focused off of one face of the prismatic mirror onto a split spherical objective lens. For isotope measurements, the multipass optical cell has a total optical path length from about 6 meters to about 10 meters, such that from about 40 to about 95 percent of the beam intensity is absorbed.

Referring to FIG. 2, sample cell 108 preferably includes a temperature control 250 and a temperature conditioner 252. Temperature control 250 monitors the temperature of sample compartment 254. Temperature conditioner 252 adjusts the temperature of sample compartment 254 to maintain the temperature within a desired range. In a preferred embodiment, temperature conditioner 254 is a resistive heating element, such as an electrically insulated metal wire, wrapped around sample compartment 254. Sample compartment 254 can be made from, for example, aluminum.

Referring to FIGS. 2 and 3, sample cell 108 preferably includes gas inlet 256 and gas outlet 258. Inlet 256 and outlet 258 connect to gas regulation apparatus 110. In a preferred embodiment of a multipass sample cell, described in detail below, inlet 256 connects with an opening that directs the inlet gas down the sample tube roughly symmetrically around the circumference of the tube to prove relatively laminar flow and correspondingly rapid and uniform filling of the sample cell. Referring to FIGS. 2 and. 3, in a preferred embodiment gas regulation apparatus 110 includes an inlet tube 270 and a dehumidifier 272 connected to gas inlet 256. Dehumidifier 272 can simply be a tube filled with silica gel desiccant, or dehumidifier 272 can be constructed from a semipermeable water absorbing membrane, suitable membranes are available from Neomax Corp., Minneapolis, Minn.

Inlet tube 270 preferably is connected to two valves 274, 276. Valve 274 controls the flow of a gas sample into tube 270. Valve 274 can be further connected to inlet 278, which can be a mouth piece for direct introduction of a breath sample or a gas storage container, such as a mylar balloon, for the indirect delivery of a stored breath sample. Additional valves can be included for the introduction of additional gas samples for processing in series with the first gas sample. Valve 276 is connected to a purge gas inlet 280. Purge gas inlet 280 can lead to an opening for the introduction of air into tube 270 or it can be connected to a gas tank of a suitable purge gas, such as nitrogen.

Gas regulation apparatus 110 generally includes a pressure sensor 282 connected to a measurement tube 284 leading to sample compartment 254. Suitable pressure sensors include, for example, model MPX5100AP manufactured by Motorola, Inc. and distributed by Newark Electronics, Minneapolis, Minn. Pressure sensor 282 is used to maintain the sample pressure at a predetermined value in preparation for and during the spectroscopic measurements. For isotope measurements the pressure in the cell generally is kept between about 50 kPa and about 100 kPa.

Gas regulation apparatus 110 generally includes a third valve 286 connected to outlet 258. Valve 286 is opened during the purge of sample compartment 254 before sample runs and can be closed once a gas sample is within sample compartment 254. Valves 274, 276, 286 can be controlled to establish the pressure as measured with pressure sensor 282 within a desired range. Gas regulation apparatus 110 also includes a pump 288, which can be located after valve 286 or at other positions within gas regulation apparatus 110. Suitable pumps include, for example, Precision Diaphragm Pumps, series 050.70-1212V from ACI Medical, Inc., San Marcos, Calif. Gas regulation apparatus 110 also generally includes one or more flow meters at a suitable location, for example leading into gas inlet 256, to measure flow into and out from cell 108.

Infrared detector 112 can include a single detector element 188, as shown in FIG. 7A. As described above, light dispersing element 180 is mounted on a pivoting mount 182 to vary the wavelength window falling on light sensitive element 188. Alternatively or in addition, light sensitive element 188 can be mounted on a movable platform 292 such that light sensitive element 188 can be moved within the spatially dispersed light beam to select a particular wavelength window to fall upon light sensitive element 188. Detector 112 can include a plurality of light sensitive elements 194 or sets of adjacent light sensitive elements to detect a plurality of wavelength windows simultaneously, as shown in FIG. 7B. In preferred embodiments, the light sensitive elements have dimensions from about 0.5 mm×3 mm to about 3 mm×3 mm to absorb wavelengths over the desired wavelength windows. Suitable infrared sensitive detector elements include, for example, Pb—Se detectors, such as Pe-3-33 detectors from EG&G-Judson, Montgomery, Pa., and pyrolelectric detectors, such as Series 404 detectors from Eltec Instruments, Inc., Daytona Beach, Fla. As shown in FIG. 7C, detector 112 can include detector array 196. Suitable detector arrays include, for example, lead-selenide (Pb—Se) detector arrays, such as model AR-170 from Eltec Instruments.

Referring to FIG. 3, detector 112 can further include a transformer 294 to generate voltages required by the light sensitive elements/arrays, if needed, and a thermoelectric (TEC) controller 296. Suitable TEC controllers are available from EG&G-Judson. TEC controllers cool Pb—Se detectors to improve their sensitivity. Lead-selenide detector arrays generally use a voltage converter to produce generally an about 100 V voltage bias.

Processor 114 preferably includes a preamplifier 300, a lock-in amplifier 302, a controller 304, and a computer 306. Preamplifier 300 receives the output from detector 112 and amplifies the signal. The output from the preamplifier 300 is directed to lock-in amplifier 302. Suitable pre-amplifiers include, for example, model PA-8200 from EG&G-Judson. Lock-in amplifier 302 amplifies the signal accounting for the modulation of the infrared light by modulator 210 to decrease the noise. Suitable lock-in amplifiers include, for example, model 5106 from EG&G Instruments, Oak Ridge, Tenn. Controller 304 can be a microcontroller board, such as model SAT-V41 from WinSystems Inc., Arlington, Tex. The controller generally includes appropriate analog and digital inputs and output, output drivers, analog-to-digital converters, a microprocessor and suitable memory. Controller 304 can be connected, for example, by way of an RS-232 serial port to a computer, which preferably is a personal computer running a suitable data management program. Computer 304 is connected to suitable output devices 308, as shown in FIG. 4.

B. Multipass Optical Cell

Figure 8:
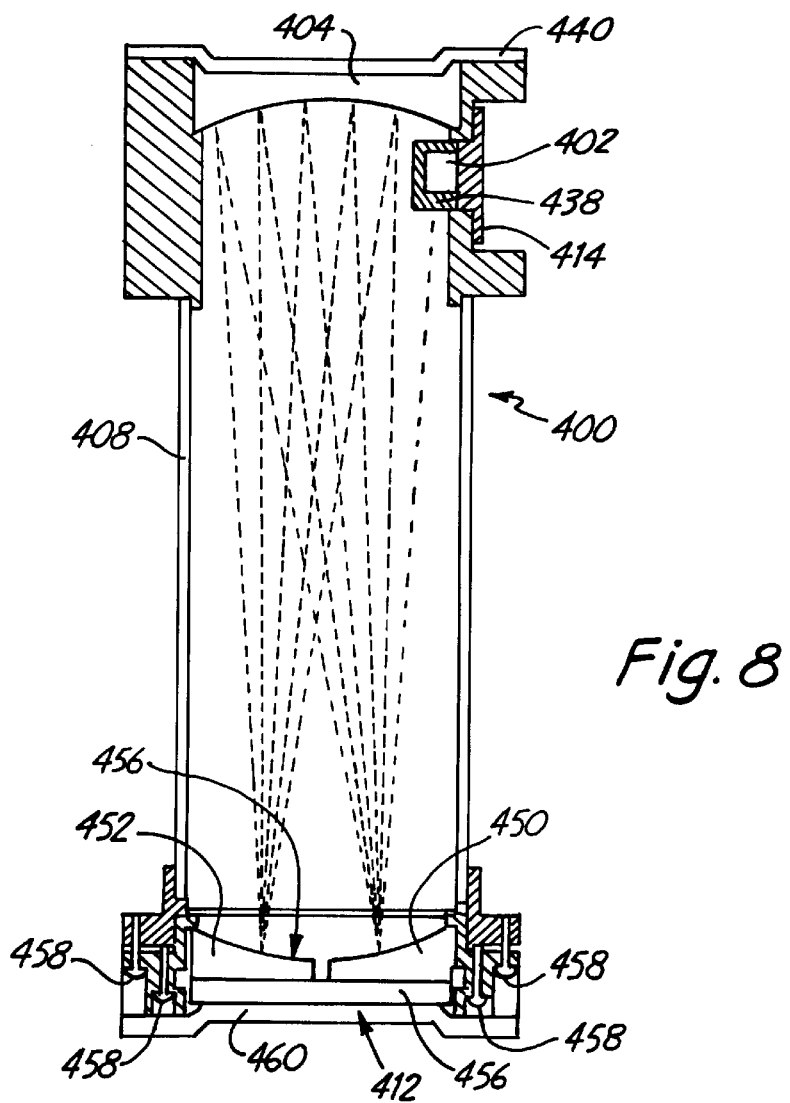
FIG. 8 is a sectional side view of an embodiment of a multipass optical cell, where the section is taken to bisect a prismatic mirror that directs the initial beam toward an objective mirror.
Figure 9:
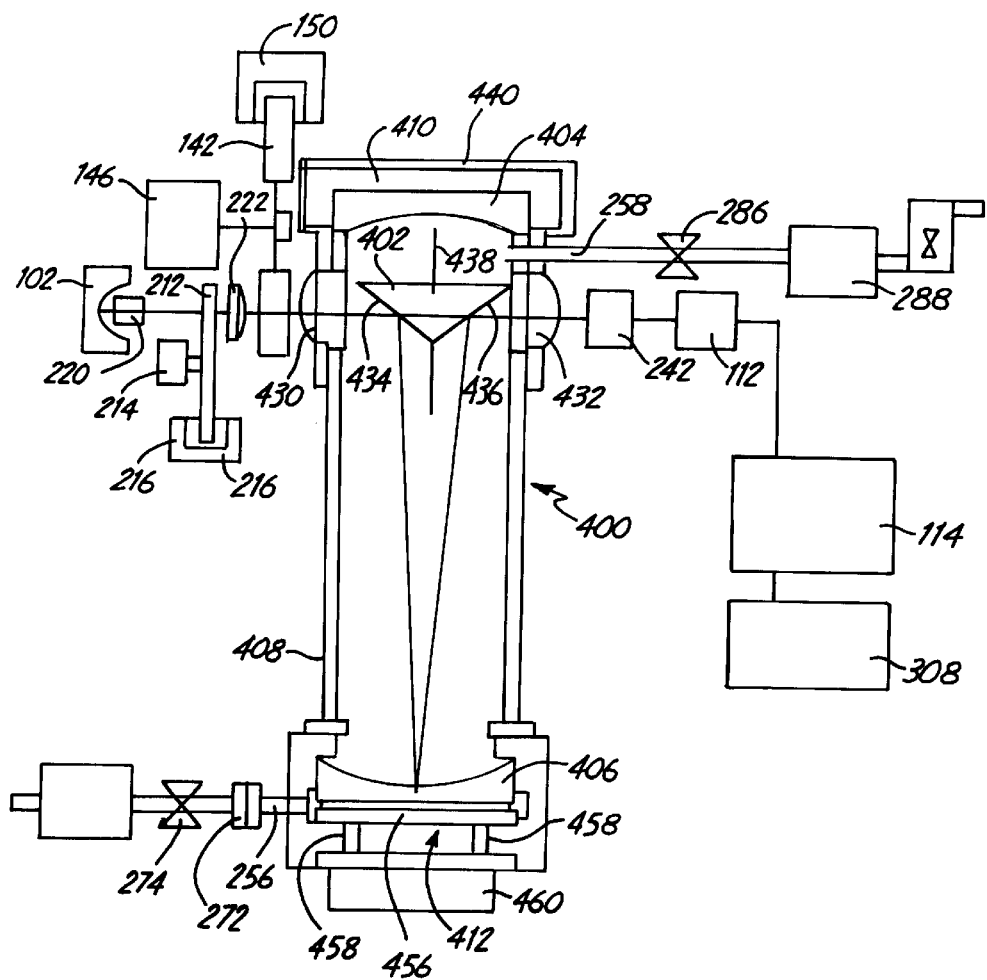
FIG. 9 is a sectional top view of the multipass optical cell of FIG. 8 forming part of an infrared spectrometer for isotope ratio evaluation, where the section is taken through the center of the prismatic mirror and through a top segment of a segmented mirror.

Referring to FIGS. 4, 8 and 9, a preferred embodiment 400 of a multipass optical cell includes a prismatic mirror 402, a spherical field mirror 404 and a split spherical mirror 406. Generally, multipass cell 400 includes a casing 408 that encloses mirrors 402, 404, 406 in a gas tight environment. For convenience, casing 408 can be generally cylindrical and enclosed at or near mounts 410, 412, which support, respectively, spherical mirror 404 and split spherical mirror 406.

Figure 10A:
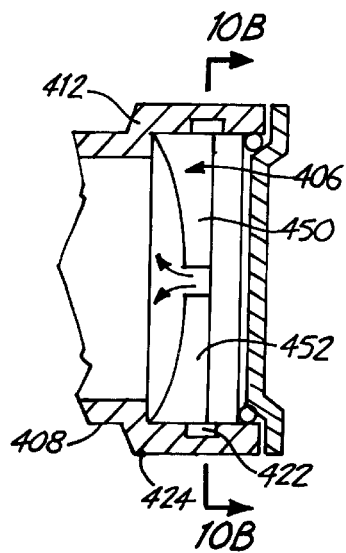
FIG. 10A is a fragmentary, sectional side view of a preferred embodiment of a multipass cell showing a gas input configuration, the section is taken through the center of a split mirror.
Figure 10B:
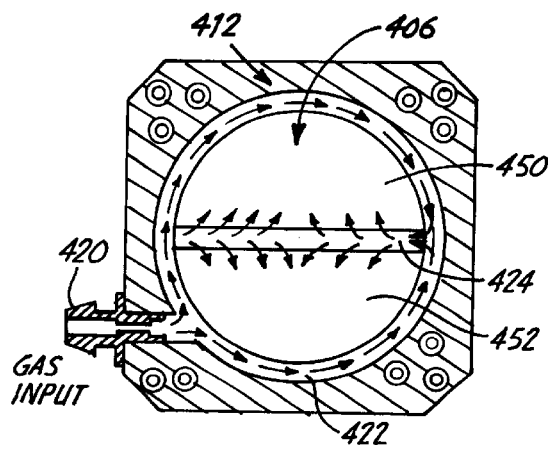
FIG. 10B is sectional from view of the multipass cell in FIG. 10A taken along the line B—B.

Casing 408 includes a gas inlet 256 and gas outlet 258 and connections for pressure measurements. A particularly preferred embodiment of gas inlet 256 leads to an opening that surrounds split mirror 406, as shown in FIGS. 10A and 10B, such that gas is flowed from the end of cell 400 for rapid filing and purging of cell 400. Gas inlet 420 is in fluid communication with a channel 422 that encircles split mirror 406. Channel 422 opens into groove 424 between the segments of split mirror 406.

Prismatic mirror 402 can be mounted. permanently along casing 408 near spherical field mirror 404. Alternatively, prismatic mirror can be attached to a cap 414 that screws reversibly into casing 408 to form a gas tight seal. Cap 414 can be removed to provide easy access for cleaning and/or replacement of prismatic mirror 402.

Casing 408 includes windows 430, 432 to provide for the introduction of infrared light through window 430 and the transmission of infrared light from cell 400 through window 432. Windows 430, 432 are at least partly transparent to infrared light and can be fabricated from $CaF_2$. In a preferred embodiment, windows 430, 432 are mounted along a linear path, such that the two holes in casing 408 for mounting, respectively, windows 430, 432 can be drilled straight through casing 408. If windows 430, 432 are mounted near spherical field mirror 404, prismatic mirror 402 can be mounted directly between windows 430, 432. Alternatively, light can be directed through windows 430, 432 at an angle toward prismatic mirror 402.

Prismatic mirror 402 is mounted near field mirror 404, as shown in FIGS. 8–10. Prismatic mirror 402 has a first face 434 oriented toward window 430 and a second face 436 oriented toward window 432. The angle between first face 434 and second face 436 is selected to reflect the infrared beam approximately along the curve at the intersection of split mirror 406 and the plane bisecting first face 434 and second face 436 of prismatic mirror 402. The angle between faces 434, 436 will be larger than 90 degrees if prismatic mirror 402 is directly between windows 430, 432. Prismatic mirror 402 is tilted relative to the line connecting the centers of field mirror 404 and objective mirror 406 such that the reflected infrared beam strikes a desired point on split mirror 406, as shown in FIGS. 8 and 11A.

Prismatic mirror should not be so large that it blocks reflections directed from split objective mirror 406 to spherical field mirror 404. For reasonable cell dimensions, prismatic mirror has an edge between faces 434, 436 with a length between about 5 mm and about 20 mm. Preferably, a shield 438 is attached to prismatic mirror 402 to block light from passing between window 430 to window 432 without reflecting from mirrors 404, 406, as shown in FIGS. 8 and 9. Shield 438 can be attached to prismatic mirror 402 by cutting a groove around prismatic mirror 402 or by using mounts along the edges of shield 438 that can be glued or the like to prismatic mirror 402. Shield 438 does not need to be placed exactly along the plane bisecting faces 434, 436.

Spherical field mirror 404 generally is mounted near one end of casing 408. Mirror 404 can be secured, for example glued, to mirror mount 410, which can be integrated into end cap 440 that forms the end of cell 400. Spherical mirror 404 has a focal length approximately equal to the distance between spherical field mirror 404 and split objective mirror 406 such that light remains focused while making multiple reflections through cell 400. For reasonable cell dimensions, spherical mirror 404 has diameters between about 30 mm and about 150 mm.

Split spherical mirror 406 involves two sections of a spherical mirror that are spaced apart from each other to form an upper segment 450 and a lower segment 452, as shown in FIGS. 4 and 8. Upper segment 450 and lower segment 452 are secured, such as by gluing, to a mounting piece 456. The spherical mirrors used to form upper segment 450 and lower segment 452 preferably each have a radius of curvature approximately equal to the distance between field mirror 404 and objective mirror 406.

To obtain the maximum number of reflections within the cell, the center of curvature of upper segment 450 is positioned approximately at the center of field mirror 404. In contrast, the center of curvature of lower segment 452 is shifted downward relative to the line connecting the center of field mirror 404 and the center of curvature of field mirror 404. This shift in centers of curvature between the upper and lower segments is depicted in FIG. 11B, where the center of curvature of upper segment 450 is labeled "1" and the center of curvature of lower segment 452 is labeled "2". The amount of shifting of the centers of curvature of upper segment 450 and lower segment 452 affects the number of reflections in the multipass cell 400, as described further below. Generally, the shift ranges from about 1 mm to about 10 mm, and more preferably from about 2 mm to about 5 mm. The center of curvature of field mirror 404 is shown in FIGS. 12A and 12B as curvature "F".

A straightforward way of producing objective mirror 406 involves the splitting of a mirror equivalent to spherical field mirror 404. The two split pieces of the mirror are separated and secured to mounting piece 456 to form one mirror unit with separated centers of curvature of the two segments. Mounting piece 456 can be positioned to place the centers of curvature of upper segment 450 and lower segment 452 relative to spherical mirror 404 roughly along the plane bisecting faces 434, 436 of prismatic mirror 402. In principle, objective mirror 406 can be produced using multiple cuts on a single mirror or using different mirrors as starting material, but due to amplification of minor variations and difficulties with respect to aligning the centers of curvature, these alternative approaches are extremely difficult to apply. For infrared light, the mirror surfaces of mirrors 402, 404, 406 can be produced with aluminum or gold coatings, preferably with a thin protective coating of, for example, sapphire ($Al_2O_3$), which can be deposited, for example, electrolytically or by electron beam evaporation.

Split objective mirror 406 is secured in mount 412. Mount 412 preferably includes adjustments to tune the orientation of split objective mirror 406 relative to field mirror 404. In preferred embodiments, the center of curvature of upper segment 450 and lower segment 452 are approximately symmetrically distributed around the center of spherical field mirror 404 along the plane bisecting faces 434, 436 of prismatic mirror 402, as depicted in FIG. 11B. Alternatively, split objective mirror 406 can be tilted to shift the centers of curvature of upper segment 450 and lower segment 452 along the plane bisecting faces 434, 436, where the tilting generally reduces the number of reflections within cell 400. In one embodiment, mount 412 includes four adjustable screws 458 that provide for small changes in the orientation of mount 412 with split objective mirror 406. Other suitable adjustable mounts can be used. Alternatively or in addition, mount 410 for spherical field mirror 404 can include adjustments for the orientation of mirror 404. Mount 412 generally is secured at or near endcap 460 forming an end of cell 400.

While the description herein concentrates on reflecting infrared light for isotope measurements, multipass cell 400 can be used for wavelengths over other portions of the electromagnetic spectrum, such as visible or ultraviolet light. The material for the windows and mirrors can be straightforwardly modified for the desired light wavelengths. Similarly, while the applications described herein concentrate on transmission wavelength windows or relatively broad band radiation, multipass cell 400 can be used to reflect monochromatic light, such as laser light, through a gas sample.

Referring to FIGS. 11A, 11B, 12A and 12B, input light reflects from prismatic mirror 402 at point 470 to upper segment 450 of split mirror 406. The distance "d" of point 470 from the plane through the center of spherical mirror 404 should be less than about one tenth of the radius of curvature of spherical mirror 404. The initially reflected light strikes upper segment 450 at point 472, the location of which depends on the tilt of prismatic mirror 402.

The light then reflects between spherical field mirror 404 and split objective mirror 406 forming a reflection pattern on field mirror 404 as indicated in FIG. 11B. The position $X_1$ depends on the aim of the incident beam onto prismatic mirror 402. Due to the shifts in the centers of curvature of segments 450, 452 that results from the split of segments 450, 452, the reflection points on field mirror 404 shift, for example, as indicated in FIG. 11B for one set of parameters. In FIG. 11B the numbers indicate the sequential reflection points in order of increasing numbers. Thus, in this embodiment, the light reflects 30 times through sample cell 400; this 30 passes gives 14 images on field mirror 404. Point 16 corresponds to reflection off of face 436 of prismatic mirror 402, which deflects out from multipass cell 400 through window 432.

The adjustment of the angle between the faces of prismatic mirror 402 and the tilt of prismatic mirror 402 are significant alignments for obtaining desired results from multipass cell 400. The number of passes N through multipass cell 400 is given by $N=(4Y_1/s)+2$, where s is the shift in the center of curvature of segments 450, 452, as shown in FIG. 11B, and $Y_1$ is the shift of the incident light beam, i.e., the first reflection point $Y_1$ of FIG. 11B, relative to the center of curvature #1 on field mirror 404, as shown in FIG. 11A. The tilt angle (f) and the mirror angle (z) between the faces of prismatic mirror 402 can be related to the coordinate of the incident beam on the mirror face and the initial reflection point on split mirror 406, as follows:

$$z=90°+\arcsin(X_p/((A-d+H_1)^2+(X_p-X_m)^2+(Y_p-Y_m)^2)^{0.5})$$

and $$f=\arcsin((Y_p-Y_m)/((A-d+H_1)^2+(Y_p-Y_m)^2)^{0.5}),$$

where $A=R-(H_1-H_m)$, R is the radius of curvature of field mirror 404. $X_p$ and $Y_p$ are defined by the point on the prismatic mirror 402, $X_p=(X_1-X_m)\cdot(A-d+H_1)/A$, $Y_p=(Y_1-Y_m)\cdot(A-d+H_1)/A$. $X_1, Y_1, H_1$ are defined by the first point on the prismatic mirror surface, and $H_1$ equals to $H_1=R-(R^2-(X_1^2+Y_1^2))^{0.5}$. $X_m$ is the distance between the center of curvature F at the center of split objective mirror 406 and the first reflection point of upper segment 450. $Y_m$ is zero in preferred embodiments where the first reflection point on the objective mirror is in the plane defined by the bisection of the prismatic mirror. Parameters for two specific configurations of multipass optical cell 400 are presented in Table 2.

TABLE 2

|  | 1 | 2 |
|---|---|---|
| R | 250 mm | 200 mm |
| $X_1$ | 6.33 mm | 6.33 mm |
| $Y_1$ | 17.5 mm | 17.5 mm |
| s | 2.5 mm | 2.5 mm |
| d | 11.06 mm | 11.33 mm |
| Total Optical Path | 7.5 m | 6.0 m |
| z | 91° 30' | 91° 50' |
| f | 1° 40' | 1° 45' |

Figure 13:
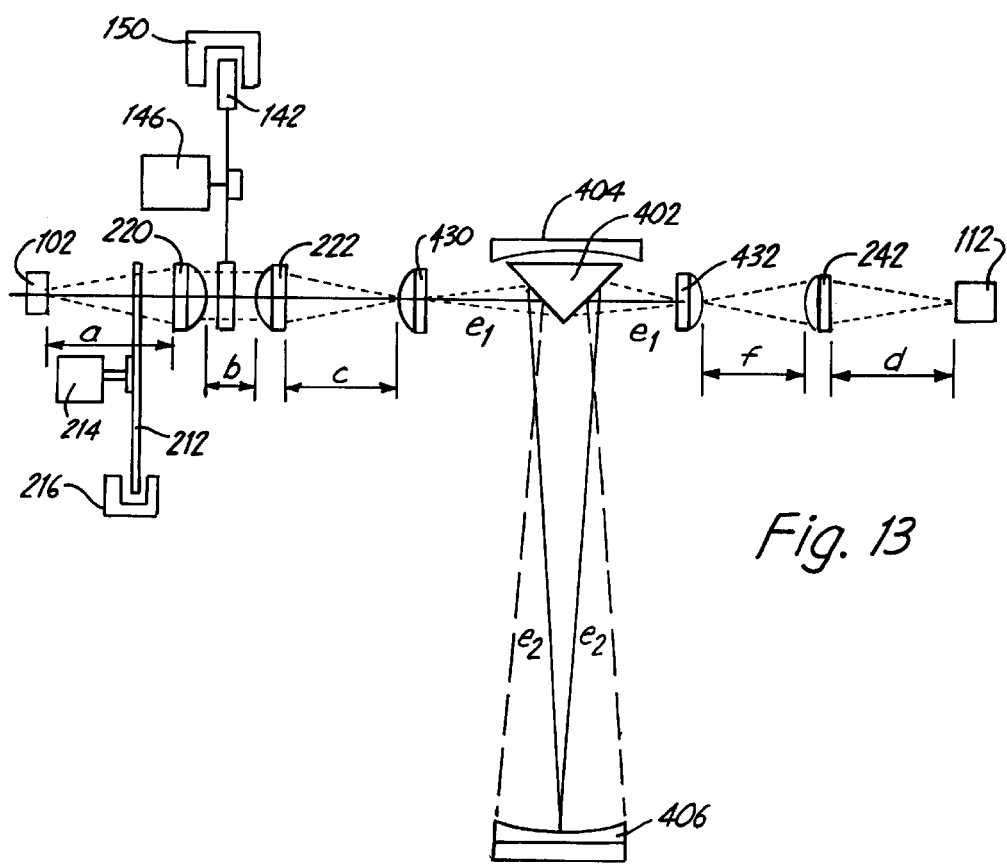
FIG. 13 is a top view within an infrared spectrometer with a preferred embodiment of a multipass optical cell, where structure is removed to expose the placement of optical components.

While the multipass optical cell with a split objective mirror can be used in a variety of optical devices, the multipass optical cell, in particular, can be used effectively in the construction of an infrared spectrometer for the measurement of isotope ratios. An infrared spectrometer for isotope ratio determination with a multipass cell having a split objective mirror is shown in FIG. 13, where enclosures have been removed to expose the placement of the optical components. In this embodiment, window 430 and 432 are convex spherical lenses made from calcium fluoride ($CaF_2$) with a diameter of 12.7 mm, a center thickness of 3 mm and a focal length of 32 mm. Optical elements 220, 222 and 242 are convex spherical lenses identical to windows 430, 432. Given these optical elements, the configuration preferably has the following distances: a—26 mm, b—8 mm, c—48 mm, f—5 mm, and $(l_1+l_2)=R$—200 mm, where R is the radius of curvature of field mirror 404 and objective mirror 406.

C. Evaluation of Isotope Ratios

The evaluation of isotopic ratios is exemplified using carbon dioxide as an example. The evaluation of isotopic ratios for other compounds using appropriate wavelength windows for the particular compound can be generalized straightforwardly from this example. The basic idea is to describe the optical densities resulting from absorption of light at particular wavelengths in terms of the concentration of the particular species in the sample that absorb at the particular wavelength.

Optical densities for analytical wavelengths have to be corrected because of possible fluctuations in the infrared source, infrared detector, ambient temperature, and optical transmission of optical parts. A suitable way to correct possible errors involves obtaining calibration values. To obtain the calibration values, voltage signals for each analytical wavelength and for a reference wavelength are measured with the cell filled with air or nitrogen. When the cell is filled with sample gas, the voltage signals are measured again for the analytical wavelengths and the reference wavelength. For example, for the measurement of carbon dioxide using the preferred wavelengths discussed above, the optical densities for the analytical wavelengths are calculated as follows:

$$D_{4.42}=\log_{10}\frac{(^0u_{4.42}\cdot{^s}u_{3.90})}{(^0u_{3.90}\cdot{^s}u_{4.42})}$$

$$D_{2.68}=\log_{10}\frac{(^0u_{2.68}\cdot{^s}u_{3.90})}{(^0u_{3.90}\cdot{^s}u_{2.68})}$$

$$D_{2.58}=\log_{10}\frac{(^0u_{2.58}\cdot{^s}u_{3.90})}{(^0u_{3.90}\cdot{^s}u_{2.58})}$$

$^0U_{4.42}, {^0}U_{3.90}, {^0}U_{2.68}, {^0}U_{2.58}$ are voltage signals for wavelengths 4.42 microns, 3.90 microns, 2.68 microns and 2.58 microns, respectively, when the cell is filled with air/nitrogen. $^sU_{4.42}, {^s}U_{3.90}, {^s}U_{2.68}, {^s}U_{2.58}$ are voltage signals for wavelengths 4.42 microns, 3.90 microns, 2.68 microns, and 2.58 microns, respectively, when a sample is in the cell. If the optical system is relatively stable, the calibration can be performed about once a week.

A set of linear equations for the concentrations can be written in terms of the optical densities. Due to relatively high total absorption, corrections for nonlinearity can be performed to improve accuracy, as described below. The solution of the linear equations leads to the desired answer.

The calculation of carbon dioxide isotopic ratios is described in terms of the preferred wavelength windows described above. Water is a difficult contaminant to remove completely and a strong infrared absorber. Therefore, correction for the presence of water may be desirable at certain wavelengths. The concentration of water is related to the optical density at 2.58 microns $D_{2.58}$ as follows:

$$D_{2.58}={^{H2O}}K_{2.58}\cdot C_{H2O}\cdot L,$$

where L is the total absorption path length in the sample cell, $C_{H2O}$ is the concentration of $H_2O$ and $^{H2O}K_{2.58}$ is the absorption coefficient for $H_2O$ at 2.58 microns. The absorption coefficients are evaluated for several known concentrations of water, $^{12}CO_2$ and $^{13}CO_2$ to calibrate a particular system to account for precise optical properties of the particular system. The optical density $D_{2.58}$ is obtained from the measurements. Thus, the concentration of $H_2O$ is easily obtained from this equation since $C_{H2O}$ is the only unknown.

The absorption at 2.68 microns can be used to obtain the concentration of C-12 carbon dioxide. The optical density at 2.68 microns is given by $$D_{2.68}={^{H2O}}K_{2.68}\cdot C_{H2O}\cdot L+{^{12}}K_{2.68}\cdot C_{12}\cdot L,$$

where $C_{12}$ is the concentration of $^{12}CO_2$ and $^{12}K_{2.68}$ is the absorption coefficient of $^{12}CO_2$ at 2.68 microns. $D_{2.68}$ is obtained from the measurements. Since $C_{H2O}$ can be determined from the absorption at 2.58 microns, $C_{12}$ can be evaluated from the above equation since it is the only unknown in the equation.

The optical density at 4.42 $D_{4.42}$ provides an equation for the concentration of $^{13}CO_2$, as follows:

$$D_{4.42}={^{12}}K_{4.42}\cdot C_{12}\cdot L+{^{13}}K_{4.42}\cdot C_{13}\cdot L,$$

where $C_{13}$ is the concentration of $^{13}CO_2$ and $^{13}K_{4.42}$ is the absorption coefficient of $^{13}CO_2$ at 4.42 microns. $D_{4.42}$ can be obtained from the infrared measurements. Then, $C_{13}$ is the only unknown assuming that $C_{H2O}$ and $C_{12}$ have been evaluated from measurements at 2.58 microns and 2.68 microns. The desired isotopic ratio is given by $C_{13}/C_{12}$. Measured optical densities, $D_{4.42}$, $D_{2.68}$, and $D_{2.58}$ may show minor nonlinearity with concentration. Correction for this minor non-linearity can be accounted for empirically by the following equations $$^{corr}c_{13} = a_{13} \cdot {}^{meas}c_{13} + b_{13} \cdot ({}^{meas}c_{13})^2$$

$$^{corr}c_{12} = a_{12} \cdot {}^{meas}c_{12} + b_{12} \cdot ({}^{meas}c_{12})^2$$

where $^{meas}c_{13}$ and $^{meas}c_{12}$ are the measured concentrations of $^{13}CO_2$ and $^{12}CO_2$, $^{corr}c_{13}$ and $^{corr}c_{12}$ are the corrected concentrations of $^{13}CO_2$ and $^{12}CO_2$ and $a_{13}$, $b_{13}$, $a_{12}$ and $b_{12}$ are correction coefficients found from calibration measurements performed with known samples.

Measurements at other wavelengths can be used to evaluate internal consistencies or to improve accuracy. If $C_{13}$ and/or $C_{12}$ are evaluated by different approaches using different wavelength measurements, the resulting values can be averaged to improve the accuracy of the ultimate isotopic ratios.

D. Carbon Dioxide Isotope Measurement From Breath Samples

Carbon dioxide is a by-product of aerobic metabolism. Thus, the generation of carbon dioxide is diagnostic of metabolic activity. If particular organisms or metabolic functions of interest specifically metabolize certain substrates, the carbon dioxide by-products of these specific substrates can be monitored to detect the metabolic activity of the specific cells or organisms of interest. Examples of specific substrates that are useful to detect certain conditions are presented in Table 3.

TABLE 3

| Substrate | Metabolic Probe |
|---|---|
| urea | H. pylori |
| triglycerides | pancreatic function/lipase function |
| lactose | lactase activity |
| octanoic acid | measurement of stomach emptying times |
| methacetin/aminopyrin | liver function |
| xylose | bacterial overgrowth in small intestine |
| glucose | malabsorption of monosaccharides |
| triolein/hiolein | malabsorption of fats |
| glycocholic acid | bile acid circulation |
| phenylalanine | phenylketonuria |
| palmitate | fatty acid metabolism |
| leucine | amino acid metabolism |

In most circumstances, background metabolic activity provides a significant. background of carbon dioxide from which to distinguish the carbon dioxide produced from a specific substrate. For example, a patient, preferably a mammalian patient, especially a human patient, produces carbon dioxide that must be distinguished from carbon dioxide produced from a specific substrate that is metabolized by an infectious organism or a specific cellular function. Similarly, air contains some carbon dioxide that adds to the background. The infrared measurements described herein provide an alternative to the use of isotope ratio mass spectrometry, which is very sensitive but requires complex and expensive equipment.

To distinguish carbon dioxide produced from a specific substrate from other. background carbon dioxide, the substrate can be enhanced in isotopes of carbon. While the substrate can be enhanced in the proportion of either $^{14}C$ or $^{13}C$, $^{13}C$ has the advantage of not being radioactive. Thus, $^{13}C$ enhanced substrates can be used without handling precautions needed for radioactive species. Naturally occurring carbon contains about 1.1% $^{13}C$. In preferred embodiments, the substrate is enhanced to contain about 99 percent $^{13}C$ carbon.

In clinical use, generally from about 40 milligrams to about 200 milligrams of a substrate is administered to the patient. A suitable period of time to allow for the metabolism of the substrate may vary with the particular type of function being probed. For the detection of H. pylori using orally administered $^{13}C$ enhanced urea, the patient's breath generally is monitored from about 10 minutes to about 90 minutes after consumption of the isotopically enhanced substrate.

The air exhaled by the patient generally has from about 3 to about 5 atomic percent $^{12}CO_2$. If the patient does not have an active infection and the substrate is not metabolized, the exhaled air has about 0.03 to about 0.05 atomic percent $^{13}CO_2$ due to natural isotopic abundance and an isotopic ratio of $^{13}CO_2$ to $^{12}CO_2$ of about 0.01125. If the patient has an active infection of H. pylori, the exhaled air has an isotopic ratio of $^{13}CO_2$ to $^{12}CO_2$ from about 0.01132 to about 0.01163, in preferred embodiments, due to metabolism of the isotopically enhanced urea substrate.

A procedure for the evaluation of isotopic ratios in carbon dioxide from a breath sample can be described with particular reference to the embodiments shown in FIGS. 2, 9 and 13. First, the spectrometer is turned on and allowed to warm up for at least about 1 minute to about 5 minutes. Controller 304 sends logical signals to open input and output valves 278, 280, 286 and to switch on pump 288. A gas with a small concentration of carbon dioxide (air or nitrogen) is pumped for about 30 second or more through the cell to purge the cell.

Then, controller 304 stops pumping, and closes all the valves. Controller 304 then initiates infrared absorption measurements for calibration with air or nitrogen in the cell. The infrared radiation from IR-emitter 130 is modulated with chopper 212, and optical elements 220, 222 direct the light through filters of filter wheel 142 to window 430. Stepper motor periodically changes the filters in the optical path for measurements at all selected analytical and reference wavelengths. The infrared radiation that is introduced into multipass cell 254 is directed by prismatic mirror, two segment objective mirror and field mirror at the output window after multiple reflections within multipass cell 254.

From the output window of the multipass cell, the infrared radiation is directed by optical element 106 to photodetector 188. The signal of photodetector 188 is amplified with preamplifier 300 and lock-in amplifier 114, which receives synchronous signals from optical sensor 216. Controller 304 measures voltage signals from the lock-in amplifier. After a stable measurement is obtained from the lock-in amplifier, controller 304 sends a logical signal to stepping motor drive 148 for changing the filter by rotating filter wheel 142 to the next position. Results of measured voltage signals for all the chosen wavelengths are saved in memory for use as calibration values.

To initiate sample measurements, samples 1 and 2 are connected to gas inputs 278 and 280, respectively. Controller 304 sends logical signals to open input valve 278 and output valve 286 and to switch on pump 288 for 15 seconds to fill cell 254 with gas sample 1. The infrared absorption measurements are repeated for all of the chosen analytical and reference wavelengths. Controller 304 then sends logical signals to open input valve 280 and output valve 286 and to switch on pump 288 for about 15 seconds to fill cell 254 with gas sample 2. The infrared absorption measurements are repeated for all chosen analytical and reference wavelengths. The isotopic ratio for gas sample 1 and gas sample 2 are evaluated according to suggested equations provided above. The difference in isotopic ratio between the two samples is displayed or printed. Using this approach and the apparatus described above, the isotopic ratio for a gas sample can be performed with reasonable accuracy in about 1 to about 2 minutes with a Pb—Se detector and in about 12 to about 15 minutes with a pyroelectric detector, once calibration values have been obtained.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A multipass optical cell comprising:
   a field mirror having a focal length and a center axis;
   a two segment objective mirror generally facing the field mirror wherein the two segments are displaced from each other to move their respective focal points away from each other; and
   a prismatic mirror displaced from the field mirror by less than about 20 percent of the focal length of the field mirror, wherein the edge of intersecting faces of the prismatic mirror is generally oriented toward the objective mirror and wherein the plane bisecting the two faces of the prismatic mirror pass through the two segments of the objective mirror.

2. The multipass optical cell of claim 1 wherein the field mirror comprises a spherical mirror having a radius of curvature.

3. The multipass optical cell of claim 2 wherein the segments of the objective mirror are portions of a spherical mirror having a radius of curvature approximately equal the radius of curvature of the field mirror, and wherein the distance between the field mirror and the objective mirror is approximately equal to the radius of curvature of the field mirror.

4. The multipass optical cell of claim 1 wherein the prismatic mirror is mounted adjacent the field mirror.

5. The multipass optical cell of claim 1 wherein the angle between the faces of the prismatic mirror is selected to reflect the optical path to approximately one segment of the objective mirror approximately along the intersection of the symmetry plane of the prismatic mirror and the objective mirror.

6. The multipass optical cell of claim 1 wherein a focused light beam entering the optical cell reflects between about 10 times and about 100 times within the cell prior to exit from the cell.

7. The multipass optical cell of claim 1 wherein the objective mirror has an adjustable mount that adjusts the orientation of the objective mirror.

8. The multipass optical cell of claim 1 wherein the field mirror has an adjustable mount that adjusts the orientation of the field mirror.

9. The multipass optical cell of claim 1 wherein the separation between portions of the two segment objective mirror is between about 1 mm and about 10 mm.

10. The multipass optical cell of claim 1 further comprising a generally cylindrical tube forming a sealed gas compartment surrounding the mirrors and the prism, the gas compartment having a gas inlet and a gas outlet.

11. The multipass optical cell of claim 10 wherein the cylindrical tube comprises a first window providing an optical path to the a first angled surface of the prismatic mirror and a second window providing an optical path from the other angled surface of the prismatic mirror out of the optical cell.

12. The multipass optical cell of claim 11 wherein the two windows are positioned to form a straight line optical path perpendicular to a plane through the symmetry axis of the field mirror, wherein the straight line optical path is interrupted by the prismatic mirror, and wherein the angled faces of the prism meet at an angle greater than about 90°.

13. The multipass optical cell of claim 11 wherein the windows have a curved surface.

14. The multipass optical cell of claim 1 wherein a shield opaque to infrared light extends from near the edge joining the two faces of the prismatic mirror.

15. The multipass optical cell of claim 1 further comprising a pressure sensor that monitors the pressure within the cell.

16. The multipass optical cell of claim 1 further comprising a temperature sensor and a temperature conditioner.

17. The multipass optical cell of claim 16 wherein the temperature conditioner comprises a heater including electrically insulated wire wrapped around a gas enclosure.

18. The multipass optical cell of claim 1 further comprising a pump and valves that are controlled to maintain the pressure within the cell from about 50 kPa to about 100 kPa.

* * * * *